United States Patent [19]

Carpentier et al.

[11] Patent Number: 4,647,283
[45] Date of Patent: Mar. 3, 1987

[54] IMPLANTABLE BIOLOGICAL TISSUE AND PROCESS FOR PREPARATION THEREOF

[75] Inventors: Alain Carpentier; Sophie Carpentier, both of Paris, France; Aws S. Nashef, Costa Mesa, Calif.

[73] Assignee: American Hospital Supply Corporation, Evanston, Ill.

[21] Appl. No.: 670,786

[22] Filed: Nov. 13, 1984

Related U.S. Application Data

[62] Division of Ser. No. 445,345, Nov. 29, 1982.

[30] Foreign Application Priority Data

Mar. 31, 1982 [FR] France ................. 82 04892

[51] Int. Cl.$^4$ .......................... A61F 2/02; A61F 2/06; A61F 2/24
[52] U.S. Cl. .................................... 623/11; 623/1; 623/2; 623/66; 8/94.11
[58] Field of Search ................. 3/1.4, 1.5, 1; 8/94.11; 623/1, 2, 11, 66

[56] References Cited

U.S. PATENT DOCUMENTS 4,378,224 3/1983 Nimni et al. ................. 8/94.11
4,481,009 11/1984 Nashef ........................ 3/1.5

OTHER PUBLICATIONS

Drescher; Chemical Abstract 71:48030c; "Inhib. Eff. of Metal Salts on Exp. Vas. Calcinosis", 1969.
Thomas et al.; Chemical Abstract 67:98480n; "Mineralization of Human & Bovine Tissue in Vitro"; 1967.
Urist, M. R. and Adams, J. M.; Effects of Various Blocking ReAgents Upon Local Mechanism of Calcification *Arch. Path* 81,325 (1966).
Sobel, A. E. and Burger, M.; Calcification XIV *Proc. Soc. Exp. Biol-.* Med. 87,7-3 (1954).

*Primary Examiner*—Richard J. Apley
*Assistant Examiner*—Gregory Beaucage
*Attorney, Agent, or Firm*—Bernard, Rothwell & Brown

[57] ABSTRACT

A process for the preparation of implantable biological tissue, and in particular bioprosthetic heart valves, which are prone to calcification after implantation. The process includes treatment of tissue with solutions prior to implantation which have been found effective in reducing calcification of the implanted tissue.

14 Claims, No Drawings

IMPLANTABLE BIOLOGICAL TISSUE AND PROCESS FOR PREPARATION THEREOF

This application is a division of application Ser. No. 445,345, filed Nov. 29, 1982.

BACKGROUND OF THE INVENTION

With the introduction of glutaraldehyde preservation of biological tissue, and in particular porcine bioprosthetic heart valves, it has become possible to: (a) overcome the poor performance of early formaldehyde-preserved implanted tissue valves; (b) discontinue the use of homograft valves; and (c) avoid the undesirable use of anticoagulants required to prevent thromboembolism associated with the use of non-bioprosthetic (mechanical) heart valves, especially in children. Not unlike other similarly important discoveries, however it appears that the glutaraldehyde-preserved bioprosthesis has created its own dilemma.

Although the relatively biologically inert glutaraldehyde-preserved valves of Carpentier and others have demonstrated excellent long-term durability in most instances, serious drawbacks such as tissue-fatigue and a propensity toward calcification have plagued their continued use. Moreover, it was initially contemplated that children and adolescents would be among those deriving the greatest benefit from the glutaraldehyde-preserved bioprosthetic heart valves since the anticoagulants required with mechanical prostheses could be eliminated. Results from an increasing number of recent clinical studies indicate that severe calcification of these tissues with relatively short-term failure is prevalent among children and adolescents. Thus, despite their long-term durability and overall reduced incidence of complications, these glutaraldehyde-preserved valves have been deemed by some to be unsuitable for use in children.

Calcification of tissue remains a mystery for the most part; however, it has previously been shown that various factors including calcium metabolism diseases, age, diet, degeneration of tissue components such as collagen, and turbulance are all involved to a certain extent. Recently, the occurrence of a specific calcium-binding amino acid, laid down after implantation of glutaraldehyde-preserved porcine xenografts, has been demonstrated; and it has been postulated to play a role in calcification. While calcification has been accompanied by degradative changes in the glutaraldehyde-treated collagen fibers of the implanted tissue, it remains unclear whether the dystrophic calcification is a cause or the result of tissue degeneration. Nevertheless, there has been a continued effort to elucidate the source of the calcification problem with implanted tissue, with the hope that a remedy would be soon to follow. Heretofore, neither the source or cause of calcification in biological implants nor the appropriate measures to prevent or reduce calcification in biological implants have been ascertained.

In accordance with the present invention, we have determined an underlying cause of calcification with biological implants, and in particular with glutaraldehyde-preserved valvular bioprostheses. Furthermore, we have concurrently developed procedures which effectively reduce or mitigate calcification of implanted biological tissue.

One of the underlying causes of calcification in valvular bioprostheses, noted for the first time in our immediate studies, is the presence of phosphate in contact with the tissue prior to implantation in amounts which sustain calcification after implantation. The levels of phosphate normally found in shipping media, such as balanced salt solutions (Hanks', etc.), plasma, and 0.01 to 0.10M phosphate-buffered-saline (PBS) conventionally used in glutaraldehyde-fixing solutions, all sustained calcification in tissue to varying degrees. Heretofore, the deleterious effects of phosphate in contact with biological implant tissue have not been appreciated, and accordingly researchers, clinicians and manufacturers alike have been unaware of the undesirable consequences caused by their treatment of these implants with phosphate-containing solutions; particularly because phosphate solutions such as Hanks', PBS, and glutaraldehyde-PBS are so commonly used and even highly recommended. It would therefore be understandable why unwittingly the interchangeability of PBS and bicarbonate buffers (having similar buffering capacities and pH ranges) might have been recommended for tissue storage resulting in sporadic substitution for phosphate-containing media. Moreover, in some instances, even bicarbonate-buffered tissue storage media contained high levels of phosphate. Since the deleterious consequences of maintaining tissue implants in contact with phosphate were unknown, there was no deliberate intent on the part of clinicians or manufacturers of bioprostheses to avoid contacting the tissue with phosphate solutions.

In accordance with the present invention, we have developed processes which effectively reduce calcification of implanted biological tissue. These processes advantageously reduce the tendency of bioprostheses toward calcification and overcome some of the problems associated with the durability of xenograft heart valves.

SUMMARY OF THE INVENTION

In accordance with the present invention, disclosed is an improved process for treating biological tissue prior to implantation which results in a mitigation or reduction of calcification thereof after implantation. In accordance with one embodiment, the process comprises contacting the tissue with a phosphate-deficient solution, said solution having a level of phosphate decreased to an amount effective in reducing calcification of said tissue after implantation, said solution further being non-destructive or non-destabilizing to said tissue; and maintaining the tissue in contact with such a phosphate-deficient solution. In an alternate embodiment, the process comprises contacting the tissue with an amount of a calcium-binding competing divalent cation effective in reducing calcification of tissue after implantation; and maintaining the tissue in contact with said cation.

DETAILED DESCRIPTION OF THE INVENTION

In accordance with the present invention, it is contemplated that various types of implantable biological tissue derived from numerous animal sources and parts of the anatomy can be made resistant to calcification. Thus, the tissue can be derived from, inter alia, bovine, porcine, horse, or rabbit; and can include tendons, ligaments, heart valves, or tissue used to construct heart valves such as dura mater and pericardium. It is further contemplated that tissue used for augmentation such as skin patches, pericardial patches, aortic patches, and tympanic membranes is suitable in the present invention. We have found, in accordance with the present invention, no significant difference in the rate of calcification between porcine pericardium and porcine aortic, tricuspid, and mitral valve tissue.

Although we are primarily concerned with tissue preparations which are fixed or tanned, such as glutaraldehyde-treated heart valves, unfixed preserved tissue should benefit from our invention. In accordance with a preferred embodiment of the present invention, treated porcine heart valves or pericardial tissue fixed in glutaraldehyde and separately implanted subcutaneously in rats and rabbits, separately have unexpectedly and beneficially resulted in a sustained mitigation or reduction of calcification after implantation. This sustained mitigation of calcification provides a method of increasing the durability of implanted tissue, particularly of heart valve bioprostheses.

In accordance with one embodiment of the present invention, we have found that biological tissue maintained, prior to implantation, in a phosphate-deficient solution advantageously results in the sustained reduction or mitigation of calcification after implantation. In accordance with one embodiment of the present invention, solutions characterized as phosphate-deficient are those having levels of phosphate below a calcification-sustaining amount; that is, in an amount below the presently used level where no significant calcification reduction or mitigation is observed. Phosphate-deficient solutions are considered to include those having substantially less phosphate than the 0.01 to 0.02M phosphate-buffered-saline solutions (PBS) conventionally used for the preparation of tissue prior to implantation; and include those solutions which we have found effective in reducing or mitigating calcification after implantation. In a preferred embodiment of the present invention, these phosphate-deficient levels are below the phosphate range normally found in plasma or balanced salt solutions such as Hank's, and Earle's which is from about 0.001 to about 0.002M. Furthermore, we find it most preferable to thoroughly rinse the blood from the host tissue after extraction in order to remove or substantially reduce any phosphate in the blood from contact with the tissue.

Substantially phosphate-free solutions are those containing only trace amounts of phosphates; as in contaminating amounts found in most chemicals used in the preparation of conventional tissue-treating solutions. We have found that HEPES buffer solutions, prepared in accordance with the present invention and further described below, contain in the neighborhood of 2–4 ppm phosphate ion. Additionally, we have found that some glutaraldehyde solutions prepared in accordance with the present invention and further described below, contain in the neighborhood of 2–23 ppm phosphate ion used as stabilizers by some manufacturers. We consider these residual or trace amounts of phosphate to be inconsequential in accordance with the present invention. Substantially phosphate-free solutions are most preferred in accordance with the present invention.

In addition to avoiding a calcification-sustaining phosphate environment for the tissue prior to implantation, it is preferable to employ solutions which are non-destructive or non-destabilizing to the tissue. For example, we have found that heart valves fixed in 1% formaldehyde in water did not calcify after implantation in rats; whereas the same valves fixed in 1% formaldehyde in PBS resulted in considerable calcification during the same period. The valves treated in the formaldehyde/water solution however, showed appreciable degeneration after about one month. The treatment of the valves in formaldehyde/water, although in the absence of phosphate, adversely affect the stabilization of the tissue after implantation and should be avoided.

The phosphate-deficient solutions of the present invention include distilled water, buffer solutions, tissue-compatible compositions such as sodium chloride, saline, or combinations of these such as buffered-saline. In a preferred embodiment, the phosphate-deficient solution is unbuffered saline, and in a more preferred embodiment it is buffered saline. In all of these solutions, it is preferable to operate within a tissue-stabilizing pH range; that is, within a pH range that is not deleterious to the tissue components. A preferred pH range is from about 7.0 to about 7.6, and a more preferred pH range is from about 7.1 to about 7.4. The most preferred pH in accordance with the present invention is 7.3.

Buffers used in accordance with one embodiment of the present invention are preferably stable, non-interacting with the stabilization process, and have a buffering capacity sufficient to maintain an acceptable pH, particularly during the fixation of the tissue. The choice of the appropriate buffer, and its concentration will depend upon specific tissue preparation conditions; variations of which have been introduced by several manufacturers. Preferred buffers in accordance with the present invention include borate, carbonate, bicarbonate, cacodylate (found to be non-toxic in animals), and other synthetic, artificial, or organic buffers such as HEPES, N-2-hydroxyethylpiperazine-N'-2-ethanesulphonic acid; MOPS, morpholine propanesulphonic acid; and PIPES, 1,4-piperazinediethanesulphonic acid. We have found that tissue prepared in HEPES buffer advantageously results in a significant reduction of calcification after implantation, and is therefore most preferred in the present invention.

In the present invention, the concentration of buffer in the phosphate-deficient solution is primarily chosen to maintain the tissue in a phosphate-deficient environment or effectively replace phosphate already present in the tissue; while at the same time controlling the pH of the solution. It is important that an amount of this buffer, either alone or in combination with solutions such as saline, be used that will effectively reduce phosphate levels or maintain the immersed tissue in a phosphate-deficient environment. In a preferred embodiment, a buffer having a concentration of from about 0.001 to about 0.10M HEPES is used. In a more preferred embodiment, a buffer having a concentration from about 0.002 to about 0.050M HEPES is used. The most preferred buffer for glutaraldehyde-fixation is one having a concentration of about 0.02M HEPES.

Preferably, the buffered or unbuffered solutions, used in accordance with the present invention should not interfere with the tissue stabilizing process afforded by fixing agents such as glutaraldehyde. That is, they should not react with the fixing agent or prevent the fixing agent from achieving proper fixation of the tissue. Illustrative of this are buffers containing primary and secondary amines such as tris(hydroxymethyl)aminomethane (Tris), which are known to react with the aldehyde groups of glutaraldehyde and thus interfere with the normal tissue stabilization process. Buffers such as Tris, although substantially free of phosphate, adversely affect the stabilization of the tissue after implantation and should therefore be avoided.

In accordance with one embodiment of the present invention, we have found that transient exposure of biological tissue to a phosphate-deficient or substantially phosphate-free solution is ineffective in reducing calcification. Unexpectedly, we have found that, in one embodiment, the biological tissue must be maintained in a substantially phosphate-deficient solution from the time the phosphate is removed from contact with the tissue in any one of the various steps to a time immediately prior to implantation. For example, we have found that porcine tissue treated with either a phosphate-deficient solution or a substantially phosphate-free solution after extraction and during shipping exhibits calcification if calcification-sustaining phosphate solutions are used in the fixation and post-fixation stages of preparation. On the other hand, we have found that tissue treated with PBS, a calcification-sustaining solution, after extraction and during shipping will effect reduced calcification if substantially phosphate-free solutions are used in the fixation and post-fixation stages of preparation. Tissue treated with substantially phosphate-free solutions after extraction, during shipping, during fixation, and post-fixation storage and sterilization are maximally effective in sustaining reduced calcification.

In accordance with one embodiment of the present invention, it is preferred to maintain the biological tissue in a phosphate-deficient solution during the post-fixation period; that is from a time subsequent to fixation through storage and sterilization such as in formaldehyde, to a time immediately prior to implantation. It is more preferred to contact the biological tissue with a substantially phosphate-deficient solution during fixation and maintain the tissue in contact with such a phosphate-deficient solution to a time immediately prior to fixation. Preferably, the phosphate-deficient solution is a component of the fixation solution. It is most preferred to contact the tissue immediately after extraction with a phosphate-deficient solution; and maintain the tissue in a phosphate-deficient solution during shipping, fixation, and post-fixation storage and sterilization to a time immediately prior to implantation.

In a preferred embodiment, the tissue is contacted with a substantially phosphate-deficient solution during fixation wherein said solution is a component of the fixation solution. Buffered and unbuffered glutaraldehyde-saline solutions, preferably from about 0.2 to about 6.0 weight percent glutaraldehyde and most preferably about 0.5 to about 0.7 weight percent glutaraldehyde, are preferred in accordance with the present invention. A more preferred fixation solution comprises buffered-saline having from about 0.5 to about 0.7 glutaraldehyde. We have found that a substantially phosphate-free fixation solution comprising 0.02M HEPES-buffered-saline containing about 0.625 weight percent glutaraldehyde at a pH of from about 7.1 to about 7.5 is effective in reducing calcification after implantation and is therefore a most preferred embodiment of the present invention.

It is further contemplated that biological tissue, shipped and/or fixed in the presence of calcification-sustaining amounts of phosphate such as about 0.01–0.02M PBS, can be thoroughly rinsed or otherwise treated with a phosphate-deficient solution prior to implantation in order to remove phosphate therefrom and thus effect a reduction or mitigation of calcification in the implanted tissue in accordance with the present invention. Rinsing or treating implantable tissue containing a calcification-sustaining amount of phosphate prior to implantation is most preferably accomplished with a substantially phosphate-free solution.

In accordance with an alternate embodiment of the present invention, we have unexpectedly found that biological tissue treated with divalent cations prior to implantation, and maintained in contact with said ions advantageously reduces or mitigates calcification of the tissue after implantation. The divalent ions added to the tissue are believed to effectively compete for the calcium-binding sites in the tissue; particularly after implantation when, in at least some instances, additional calcium-binding sites are generated. We have found that by increasing the amount of divalent ions such as magnesium ions in tissue after fixation in glutaraldehyde-PBS, we have effected a sustained reduction or mitigation of calcification; whereas tissue fixed in glutaraldehyde-PBS with increased amounts of magnesium ions and subsequently exposed to additional amounts of calcification-sustaining phosphate did not exhibit a reduction or mitigation of calcification. Thus, in accordance with the present invention, it is not considered necessary to maintain the divalent cation-treated tissue in contact with a phosphate-deficient solution prior to or during treatment with the ion; however, it is preferred that the tissue be maintained in a phosphate-deficient solution after divalent ion treatment to a time prior to implantation.

In accordance with the present invention, it is contemplated that any divalent ion which effectively competes for the calcium-binding sites in the tissue will reduce calcification. Accordingly, preferred divalent cations include barium, magnesium, strontium, copper, zinc, silver, and mercury. We have found that tissue treated with barium, strontium, and magnesium ions prior to implantation effectively reduce calcification after implantation in accordance with the present invention. Magnesium ion is most preferred in accordance with the present invention.

In a preferred embodiment of the present invention the magnesium ion is derived from magnesium salt solutions; most preferably water-soluble salt solutions such as magnesium chloride ($MgCl_2$), magnesium sulfate ($MgSO_4$), and magnesium carbonate ($MgCO_3$). In the most preferred embodiment, the magnesium salt comprises magnesium ion in an amount effective in reducing or mitigating calcification of tissue after implantation. Although the concentration of the magnesium ion and the time it is in contact with the tissue can vary, we find it preferable that the tissue is substantially saturated with solutions containing effective amounts of this ion.

In accordance with the present invention, effective amounts of divalent cations such as magnesium ion in contact with the tissue are considered to be those amounts in excess of the quantities found in certain PBS, balanced salt solutions, and plasma. Conventional PBS solutions usually contain on the order of 0.001 weight percent magnesium ion; balanced salt solutions on the order of 0.002 weight percent; and the upper limit in plasma is in the order of about 0.003 weight percent. A preferred amount of magnesium ion is one that exceeds from about 0.003 to about 0.004 weight percent. The maximal amount of magnesium ion contemplated to be useful in the present invention is that level required to maintain an isotonic solution. We have found that saturating tissue with solutions containing about 0.03 percent magnesium ion has effected a reduction of calcification in tissue, and represents the preferred process. This was accomplished by immersing tissue in a 0.26 weight percent solution of magnesium chloride which affords a 0.03 weight percent solution of magnesium ions. Solutions such as balanced salt solutions, having more than about 0.003 percent magnesium ion normally found in plasma would have a similar beneficial effect and would be preferred in accordance with the present invention.

In accordance with one embodiment of the present invention, we have found that extracted porcine valvular tissue shipped in HEPES-buffered-saline, fixed in HEPES-buffered-saline containing 0.25 weight percent magnesium chloride and 0.625 weight percent glutaraldehyde, rinsed in HEPES-buffered-saline containing 0.26 weight percent magnesium chloride, sterilized in HEPES-buffered-saline containing 0.26 weight percent magnesium chloride and about 4.0 weight percent formaldehyde, rinsed and stored in HEPES-buffered-saline containing 0.26 weight percent magnesium chloride and 0.625 weight percent glutaraldehyde, until immediately prior to implantion advantageously and significantly reduces or mitigates calcification of the tissue after implantation. Thus, in accordance with one embodiment of the present invention, it is most preferred to glutaraldehyde-fix the biological tissue in a HEPES-buffered-saline solution containing an effective amount of magnesium, and maintain the solution in contact with said HEPES-buffered-saline solution and magnesium ion to a time immediately prior to implantation.

It is further contemplated, in accordance with the present invention, that biological tissue processed in the absence of effective amounts of magnesium can be rinsed in sterile solutions, such as magnesium chloride, immediately prior to implantation to effect a reduction of calcification.

The present invention is further illustrated by the following examples which are not intended to be limiting:

EXAMPLE I

Extracted porcine aortic heart valve tissue was thoroughly rinsed, shipped, fixed with 0.625 weight percent glutaraldehyde, sterilized in about 4% formaldehyde, stored at about 4° to 25° C., all in the presence of a phosphate-deficient isotonic (285±15 milliosmols) solution containing 0.885 weight percent sodium chloride at pH 7.3, rinsed in sterile saline to remove residual glutaraldehyde at a time immediately prior to implantation, and implanted in growing rabbits. The valve tissue was retrieved up to six weeks later at regular one-week intervals. After retrieval, the extent of tissue calcification was assessed by quantitatively monitoring the weight percent calcium in dried tissue using atomic absorption analysis; and histologically by visually monitoring the degree of calcification in Von Kossa-stained tissue sections. The extent of calcification was simultaneously and identically assessed for heart valve tissue which was rinsed, shipped, fixed with 0.625 weight percent glutaraldehyde, sterilized in about 4% formaldehyde, stored at about 4° to 25° C. all in the presence of an isotonic solution containing 0.02M phosphate, 0.885 weight percent sodium chloride at pH 7.3 (0.02M PBS), rinsed in sterile saline to remove residual glutaraldehyde at a time immediately prior to implantation, and implanted in growing rabbits.

Both the histologic and quantitative results indicate that the implanted valve tissue treated with the phosphate-deficient solution effected at significant reduction in calcification compared to the valve tissue treated with 0.02M PBS.

EXAMPLE II

Experiments identical to those of Example I were conducted with the exception that the tissue was implanted in mature rabbits and retrieved up to six months later at regular one-month intervals. Likewise, both histologic and quantitative results indicate that implanted valve tissue with the phosphate-deficient solution effected a significant reduction in calcification compared to the valve tissue treated with 0.02M PBS.

EXAMPLE III

Experiments identical to those of Example II were conducted with the exception that the phosphate-deficient solution further contained 0.54 grams/liter of the sodium salt of HEPES during rinsing and shipping; and 5.39 grams/liter of the sodium salt of HEPES during fixation, storage, and sterilization. Again, both histologic and quantitative results indicate that the implanted valve tissue treated with the phosphate-deficient solution effected a reduction in calcification compared to the valve tissue treated with 0.02M PBS.

EXAMPLE IV

Experiments identical to those of Example I were conducted with the exception that the phosphate-deficient solutions further contained 0.54 grams/liter of the sodium salt of HEPES during rinsing and shipping; 5.39 grams/liter of the sodium salt of HEPES during fixation, storage, and sterilization; and 2.6 grams/liter of $MgCl_2.6H_2O$ in the fixation, storage, and sterilization solutions. Again, both histologic and quantitative results indicate that implanted valve tissue treated with the phosphate-deficient solution effected a significant reduction in calcification compared to the valve tissue treated with 0.02M PBS.

EXAMPLE V

Experiments identical to those of Example IV were conducted with the exception that the tissue was implanted in mature rabbits and retrieved up to six months later at regular one-month intervals. Both histologic and quantitative results indicate that implanted valve tissue treated with the phosphate-deficient solution effected a significant and sustained reduction in calcification compared to the valve tissue treated with 0.02M PBS.

EXAMPLE VI

Experiments identical to those of Example I were conducted with the exception that the phosphate-deficient solution further contained 0.05M cacodylate buffer, and the valve was retrieved up to only two weeks later at weekly intervals. Furthermore, the extent of calcification was simultaneously and identically assessed using 0.012M phosphate, 0.885 weight % sodium chloride at pH 7.3 (0.012M PBS) prior to implantation. The histologic results indicate that the implanted valve tissue treated with phosphate-deficient solution effected a slight reduction in calcification after one week compared to the valve tissue treated with 0.012M PBS. Thereafter, mild calcification was observed.

EXAMPLE VII

Experiments identical to those of Example VI were conducted with the exception that 0.1M borate buffer was substituted for cacodylate. The histologic results were similar to those in Example VI.

EXAMPLE VIII

Experiments identical to those of Example IV were conducted with the exception that neither solution for comparison was phosphate-deficient; that is, the fixation, storage and sterilization solutions sustained 0.02M PBS instead of HEPES buffer. Both histologic and quantitative results indicate that the implanted valve tissue treated with the phosphate-containing magnesium chloride solution effected a reduction in calcification compared to the valve tissue treated without magnesium chloride.

EXAMPLE IX

Experiments identical to those of Example III were conducted in order to assess the integrity of the tissue after implantation. The results of our analysis indicate that there was no significant difference in: shrinkage temperature; Ninhydrin values; leachable uronic acid in an acid mucopolysaccharide leach; the stability of the tissue subjected to pronase digestion; histological staining; amino acid analysis; ultrastructure as assessed by transmission electron microscopy; or moisture content.

EXAMPLES X–XXII

Extracted porcine heart valve tissue was interchangeably treated with phosphate-deficient solutions and phosphate-containing solutions at various stages of processing (pre-fixing, glutaraldehyde-fixation, and post-fixation) prior to implantation in rats in order to assess the degree of calcification mitigation afforded by each stage of treatment. The results in Table I summarize our findings after up to two months in some cases after implantation. In the table, $G_p$ represents glutaraldehyde-treated tissue in 0.02M PBS; $F_{H2O}$ represents formaldehyde-treated tissue in water; $G_{water}$ represents glutaraldehyde-treated tissue in water; $F_p$ represents formaldehyde-treated tissue in 0.02M PBS; $G_{HEPES}$ represents glutaraldehyde-treated tissue in 0.002M HEPES; $G_{carbonate}$ represents glutaraldehyde-treated tissue in carbonate buffer; saline/HEPES represents 0.002M HEPES-buffered-saline; and BSS represents balanced salt solution.

EXAMPLE XXIII

Experiments identical to those of Example IV were conducted with the exception that $MgCl_2.6H_2O$ was replaced with $BaCl_2.2H_2O$ at a concentration of 2.2 grams/liter. The results indicate that barium had an effect on calcification similar to magnesium.

EXAMPLE XXIV

Experiments identical to those of Example IV were conducted with the exception that $MgCl_2.6H_2O$ was replaced with $SrCl_2.2H_2O$ at a concentration of 2.3 grams/liter. The results indicate that strontium had an effect on calcification similar to magnesium.

TABLE I

| | CALCIFICATION STUDIES IN RATS | | |
|---|---|---|---|
| Pre-Tanning | Treatment Tanning | Post-Tanning | Degree of Calcification |
| PBS | $G_p$ | phosphate | severe |
| PBS | $F_{H2O}$ | phosphate-deficient | reduced (degeneration) |
| PBS | $F_p$ | phosphate | severe (degeneration) |
| PBS | $G_{water}$ | phosphate-deficient | reduced |
| PBS | $G_{HEPES}$ | phosphate-deficient | reduced |
| PBS | $G_{carbonate}$ | phosphate-deficient | slightly reduced |
| Hank's (BSS) | $G_p$ | phosphate | severe |
| Saline/HEPES | $G_p$ | phosphate | severe |
| Hank's (BSS) | $G_{saline/HEPES}$ | phosphate-deficient | reduced |
| PBS | $G_{saline/HEPES}$ | phosphate-deficient | reduced |
| Saline/HEPES | $G_{saline/HEPES}$ | phosphate-deficient | reduced (sustained) |
| PBS | $G_p$ | $MgCl_2$—phosphate deficient | reduced (sustained) |
| PBS | $G_p$ | $MgCl_2$—$G_p$ | severe |

The present invention has been described in specific detail and in reference to its preferred embodiments; however, it is to be understood by those skilled in the art that modifications and changes can be made thereto without departing from the the spirit and scope thereof.

We claim:

1. A process for treating biological tissue prior to implantation which comprises the steps of:
   a. fixing said tissue under tissue fixing conditions;
   b. contacting said fixed tissue with a solution effective in reducing calcification of said tissue after implantation; said calcification reducing solution comprising an amount of a calcium-binding competing divalent cation effective in reducing calcification and having a level of phosphate decreased to an amount effective in reducing calcification of tissue after implantation; and
   c. maintaining the tissue in contact with a solution having said reduced level of phosphate to a time just prior to implantation.

2. A method of increasing the durability of implantable biological tissue which comprises the steps of:
   a. fixing said tissue under tissue fixing conditions;
   b. contacting said fixed tissue with a solution effective in reducing calcification of said tissue after implantation; said calcification reducing solution comprising an amount of a calcium-binding competing divalent cation effective in reducing calcification and having a level of phosphate decreased to an amount effective in reducing calcification of tissue after implantation; and
   c. maintaining the tissue in contact with a solution having said reduced level of phosphate to a time just prior to implantation.

3. The process of claim 1 wherein the divalent cation is a magnesium ion or salt thereof.

4. The process of claim 3 wherein the magnesium salt is selected from the group consisting of $MgCl_2$, $MgSO_4$, and $MgCO_3$.

5. The process of claim 3 wherein the magnesium salt is magnesium chloride.

6. The process of claim 1 wherein the tissue is treated with an amount of divalent cation sufficient to saturate the tissue.

7. The process of claim 1 wherein the biological tissue is used in the preparation of a heart valve.

8. The process of claim 5 wherein the tissue is used in the preparation of a heart valve and the concentration of magnesium chloride is about 0.26 weight percent.

9. The method of claim 2 wherein the divalent cation is a magnesium ion or salt thereof.

10. The method of claim 9 wherein the magnesium salt is selected from the group consisting of $MgCl_2$, $MgSO_4$, and $MgCO_3$.

11. The method of claim 9 wherein the magnesium salt is magnesium chloride.

12. The method of claim 2 wherein the tissue is treated with an amount of divalent cation sufficient to saturate the tissue.

13. The method of claim 2 wherein the biological tissue is used in the preparation of a heart valve.

14. The method of claim 11 wherein the tissue is used in the preparation of a heart valve and the concentration of magnesium chloride is about 0.26 weight percent.

* * * * *